United States Patent
Rippon et al.

(10) Patent No.: US 7,083,806 B2
(45) Date of Patent: Aug. 1, 2006

(54) WOUND GELS

(75) Inventors: Mark Geoffrey Rippon, Wrexham (GB); John Meadows, Wrexham (GB)

(73) Assignee: Maelor Pharmaceuticals Limited, Wrexham (GB)

( * ) Notice: Subject to any disclaimer, the term of this patent is extended or adjusted under 35 U.S.C. 154(b) by 0 days.

(21) Appl. No.: 10/275,771

(22) PCT Filed: May 8, 2001

(86) PCT No.: PCT/GB01/02016

§ 371 (c)(1),
(2), (4) Date: Jun. 26, 2003

(87) PCT Pub. No.: WO01/85845

PCT Pub. Date: Nov. 15, 2001

(65) Prior Publication Data

US 2004/0028739 A1    Feb. 12, 2004

(51) Int. Cl.
*A61K 9/14*    (2006.01)
(52) U.S. Cl. ............... 424/484; 424/486; 424/487; 424/488
(58) Field of Classification Search ............ 424/445, 424/446, 447, 449, 484, 486, 487, 488; 514/54, 514/57, 60, 78.08
See application file for complete search history.

(56) References Cited

U.S. PATENT DOCUMENTS

| | | |
|---|---|---|
| 4,920,158 A | 4/1990 | Murray et al. |
| 5,013,769 A | 5/1991 | Murray et al. |
| 5,057,308 A | 10/1991 | Hill et al. |
| 5,071,644 A | 12/1991 | Viegas et al. |
| 5,077,033 A | 12/1991 | Viegas et al. |
| 5,124,151 A | 6/1992 | Viegas et al. |
| 5,143,731 A | 9/1992 | Viegas et al. |
| 5,277,911 A | 1/1994 | Viegas et al. |
| 5,346,703 A | 9/1994 | Viegas et al. |
| 5,376,693 A | 12/1994 | Viegas et al. |
| 5,496,541 A | 3/1996 | Cutler |
| 5,603,955 A | 2/1997 | Gehrke et al. |
| 5,674,521 A | 10/1997 | Gehrke et al. |
| 5,814,031 A | 9/1998 | Mooney et al. |
| 5,840,338 A * | 11/1998 | Roos et al. ............ 424/488 |
| 5,843,575 A | 12/1998 | Wang et al. |
| 5,847,023 A | 12/1998 | Viegas et al. |
| 5,851,672 A | 12/1998 | Wang et al. |
| 5,858,535 A | 1/1999 | Wang et al. |
| 5,942,478 A | 8/1999 | Lopes |
| 6,099,950 A | 8/2000 | Wang et al. |
| 6,231,872 B1 | 5/2001 | Mooney et al. |

FOREIGN PATENT DOCUMENTS

| | | |
|---|---|---|
| CA | 1339682 | 9/1989 |
| EP | 0 041 934 A1 | 12/1981 |
| EP | 0 470 703 A1 * | 2/1992 |
| EP | 0 732 108 A2 | 9/1996 |
| GB | 1292640 | 10/1972 |
| WO | WO 93/04691 | 3/1993 |
| WO | WO 98/02196 | 1/1998 |

OTHER PUBLICATIONS

Agren, M.S. (1998), "An Amorphous Hydrogel Enhances Epitherlialisation of Wounds," *Acta Derm. Venereol.* (Stochh) 78:119-122.
Cho, C.S. (1994), "Effect of polymeric surfaces on the cloud point of poly(N-isopropylacrylamide)," *Macromol. Rapid Commun*. 15:727-732.
Winter, G.D. (1962), "Formation of the Scab and the Rate of Epithelization of Superficial Wounds in the Skin of the Young Domestic Pig," *Nature* 193:293-294.

* cited by examiner

*Primary Examiner*—Elli Peselev
(74) *Attorney, Agent, or Firm*—Greenlee Winner and Sullivan

(57) ABSTRACT

The present invention relates to hydrogels, in particular gels for use on wounds. The invention provides a gel which is better able to maintain viscosity and gel integrity when exposed to wound exudates, for example. A hydrogel comprising a poloxamer is provided. Further provided is a hydrogel comprising a cross-linked gellant, and water wherein the hydrogel comprises a poloxamer and has the capacity to absorb at least 50% further water in addition to the water already present. Suitable gellants are pharmaceutically acceptable, cross-linked, hydrophilic polymers. Hydrogels of the present invention are useful in medicine, or therapy and are in particular useful in application to epithelial lesions, especially wounds, such as accidental or surgical wounds.

28 Claims, 2 Drawing Sheets

WOUND GELS

CROSS-REFERENCE TO RELATED APPLICATIONS

This application is a U.S. National Stage application under 35 U.S.C. 371 of International application PCT/GB01/02016, filed May 8, 2001, which takes priority from United Kingdom application No. UK 0011062.7, filed May 8, 2000, both of which are incorporated by reference herein.

BACKGROUND OF THE INVENTION

The present invention relates to hydrogels, in particular gels for use on wounds.

It is known (Winter, G. D. 1962, Nature 193, pp 293–294) that healing under an occlusive dressing which maintains a moist environment is significantly better than using dry dressings, or leaving a wound open to the atmosphere.

The concept of moist healing has been applied to the management of both acute and chronic wounds. This has resulted in a significant improvement in the outcome of healing in wounds that were, by their very nature, difficult to heal. As a consequence of this, the wound care industry has seen an increase in the number of occlusive dressings designed specifically to maintain a moist wound environment. At the forefront of this technology has been the development of hydrogel dressings.

These hydrogel dressings are water and polymer combinations designed to create and/or maintain a hydrophilic microenvironment over the wound surface. The gel is in intimate contact with the wound surface, and absorbs exudate into the hydrophilic layer of gel. This prevents an accumulation of fluid at the wound surface yet keeps the cells moist. It has been demonstrated that this moist wound environment is optimal for re-epithelisation and fibroplasia.

Hydrogels can also donate water to desiccated tissue and are very useful in re-hydrating dry eschar and slough, thereby encouraging autolytic debridement. Other advantages of hydrogels are that they allow free passage of water vapour and oxygen, and the low adhesion of the gel to the wound surface allows easy removal (usually by irrigation) without damage to the underlying newly formed tissue.

Hydrogel systems for use in wound care have been described by, for example, Agren, M. S. in Acta. Derm. Venereol. 1998, 78:119–122

The problem with such known hydrogels is that exposure to fluid released from the wound causes an exponential reduction of viscosity of the gel, leading to loss of gel integrity and, if left in place on the wound, will exacerbate tissue (both wound and normal skin) maceration. Therefore, dressing changes have to be undertaken frequently to prevent this problem, which is both time consuming and expensive.

SUMMARY OF THE INVENTION

It is an object of the present invention to overcome these disadvantages, and to provide a gel which is better able to maintain viscosity and gel integrity when exposed to wound exudates, for example.

We have now, surprisingly, discovered that the polymer particles of hydrogels are capable of increased swelling and are better able to maintain viscosity upon dilution with wound exudate, when in the presence of a poloxamer. Thus, a hydrogel comprising a poloxamer is provided.

Accordingly, in a first aspect, the present invention provides a hydrogel comprising a cross-linked gellant and water, characterised in that said hydrogel comprises a poloxamer and has the capacity to absorb at least 50% further water in addition to the water already present.

It will be appreciated that a hydrogel is a gel comprising water, by definition. Hydrogels of the present invention can absorb at least 50% more water than the initial amount with which they are made. This is generally the lower end of the range, and preferred hydrogels can absorb at least a further 100% water, more preferably 150% and especially 200%. Particularly preferred hydrogels of the present invention are capable of absorbing twice their own weight of wound exudate.

Suitable gellants are pharmaceutically acceptable, cross-linked, hydrophilic polymers. By "cross-linked" is meant that the polymer is cross-linked so as to prevent any appreciable level of dissolution of gellant in water. Such cross-linking may be effected by any suitable means, and many forms of cross-linking are well known in the art.

For example, cross-linking may be effected by exposure to γ or UV irradiation when appropriate groups are present in the polymer. More generally, chemical cross-linking is convenient, and may be effected, for example, by introducing appropriate reactive bifunctional monomers into a solution of the non cross-linked polymer before initiating the reaction. Suitable cross-linking reagents for these purposes include epichlorohydrin, methylene bis acrylamide and glutaraldehyde.

The extent of cross-linking is largely unimportant, and is not critical to the present invention, provided that the gel is not unduly restricted from absorbing moisture and that the gellant does not substantially dissolve in water to any extent. Cross-linking is generally empirical and difficult to define, and the skilled person will appreciate what is necessary to cross-link a polymer sufficiently.

Various cross-linked, hydrophilic polymers are available, including polyacrylates and polysaccharides. In general, it is preferred to use cross-linked, superabsorbent carbohydrates in the present invention. Those generally commercially available are polysaccharides, derivatised to highly charge the molecule, and include, for example, cross-linked starch available from Vulca, and cross-linked carboxymethylcellulose (CMC), generally available as their sodium salts. Cross-linked sodium CMC's are commercially available under the name Aquasorb™ (Honeywell & Stein, Times House, Throwley Way, Sutton, UK). Any reference to a cross-linked polysaccharide herein is also a reference to a polysaccharide pre-cross-linked, before addition of poloxamer, unless otherwise stated. The poloxamer is not physically connected or cross-linked with the polymer of the gellant. References to polysaccharide herein should also be taken as references to other gellants, unless otherwise indicated.

More particularly, hydrogels of the present invention are useful in medicine, or therapy.

In particular, hydrogels of the present invention are useful in application to epithelial lesions, especially wounds, such as accidental or surgical wounds.

DETAILED DESCRIPTION OF THE INVENTION

Figure 1:
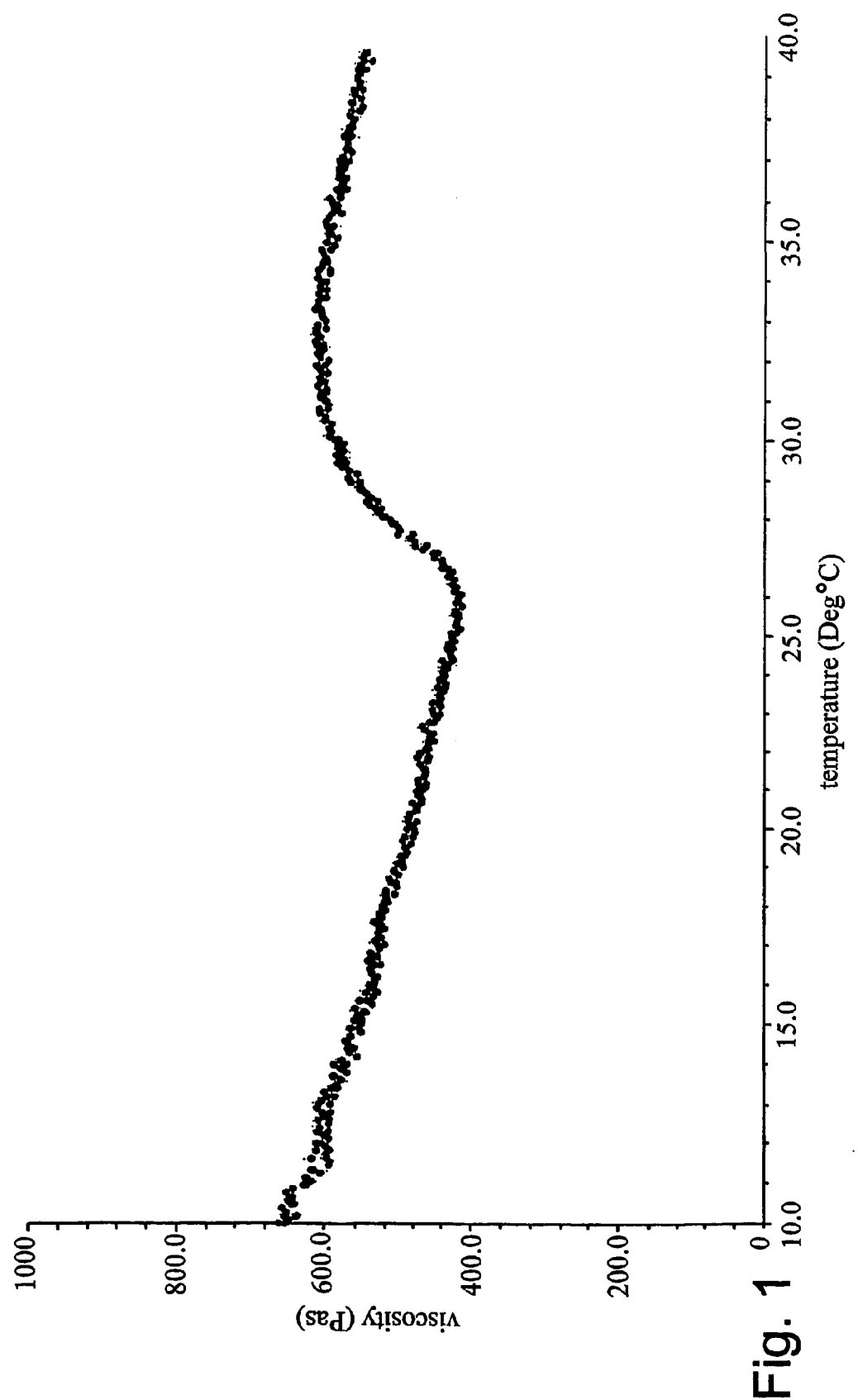
FIG. 1 shows a graph of the viscosity-temperature profile of the formulation as described in Example 1. The formulation displays an increase in viscosity at a temperature of approximately 27° C.

Wounds, or lesions, come in many forms, and virtually all are suitable for treatment with hydrogels of the present invention. In general, they are either 'dry' or 'wet', insofar as the levels of exudate they produce. In addition, they may be deep or shallow, broad or narrow, simple abrasions or multiple lesions, infected or ragged, and the skilled physician will readily determine which hydrogel of the present invention to use.

It will be appreciated the present invention further provides a method for the treatment of the human or animal body by application of a hydrogel of the present invention. Although in some preferred embodiments of the present invention the hydrogel comprises active components, the simple hydrogels of the invention are effective to prevent infection and provide an ideal microenvironment for wound healing.

A main advantage of the present invention lies the fact that the polymer particles of the hydrogel are capable of swelling more on contact with water when in the presence of a poloxamer, so that gels of the invention are able to absorb more fluid than known hydrogel systems, whilst still maintaining gel integrity.

Without being constrained by theory, we believe that a large proportion of the poloxamer molecules is actually located within the cross-linked polymer component of the hydrogel, and not just in the periparticulate neighbourhood. The evidence for this is based on viscosity-temperature profiles which indicate that the poloxamer molecules have access to approximately 85% of the solvent phase. Given that the swollen polymer particles have an effective volume fraction sufficient to gel the entire system then, in order to have access to anything like 85% of the solvent phase, the poloxamer molecules must be present within the polymer particles.

In a further aspect, the invention relates to a hydrogel suitable for use on wounds, comprising a poloxamer and a cross-linked polysaccharide.

In a yet further aspect, the invention relates to a hydrogel suitable for use on wounds, comprising a poloxamer and cross-linked carboxymethylcellulose.

Such a hydrogel is able to be used in the absence of any additional active agent, such as a drug to promote wound healing. Therefore, in one embodiment, the invention also relates to a hydrogel suitable for use on wounds, comprising a poloxamer and a cross-linked polysaccharide without any other medicinally active agent.

The present invention also relates to a hydrogel comprising a poloxamer and a cross-linked polysaccharide for use in medicine, particularly in the treatment of wounds, or use of a hydrogel comprising a poloxamer and a cross-linked polysaccharide in the preparation of a medicament for the treatment of wounds, either, preferably, for topical administration.

Additionally, the invention relates to a pharmaceutical composition comprising a poloxamer and a cross-linked polysaccharide. By the term "pharmaceutical composition" or "pharmaceutical preparation" is meant any preparation which is intended for administration to the human or animal body, whether internally or externally.

The presence of even low levels of a cross-linked polysaccharide also provides the gel with greater 'body', which can help in the gel setting, and can help thicken the gels, even where they do not set, at least not before being applied to a wound.

Hydrogels of the present invention may usefully comprise polar groups, either as part of an ingredient of the gel, or preferably as part of the cross-linked polysaccharide. It will be appreciated that the cross-linked polysaccharide will necessarily already comprise a high proportion of polar or ionic groups, such as —OH and —COOH, in order that they possess the desirable superabsorbent characteristics. If necessary, these can be further supplemented or selected by the use of appropriately derivatised monomers. For example, —OH, —CONH—, and $(CH_3)_2N$— groups are readily introduced using monomers readily apparent to those skilled in the art, and are useful to induce spreading of macrophages at the interface of the hydrogel and a wound. Materials containing —$SO_3H$ groups slightly, and materials containing —COOH groups more intensively, inhibit spreading of macrophages, and this can be useful in inhibiting fusion of macrophages into multinucleate cells.

It will be appreciated that the present invention extends to mixes of gellant and poloxamer suitable to be diluted with water to form hydrogels of the invention. More particularly, such pre-mixes preferably comprise a co-solvent, such as described below, as are suitable concentrations of ingredients.

The presence of the poloxamer molecules within the swollen polymer units would appear to produce a substantial osmotic gradient. Thus, in contrast to other hydrogels which have a greater tendency toward water donation, hydrogels of the present invention are able to not only absorb moisture from all wound types, and not just "wet" wounds, but can also absorb substantially more water, as the increased osmotic pressure swells the polymer particles with more water than would otherwise be absorbed in the absence of poloxamer.

In general, the hydrogels of the present invention absorb water at about the same rate as other gels on the market. However, the absorption rate of saline, which is representative of wound exudates, is significantly different, with hydrogels of the present invention absorbing a significantly greater amount of saline than either IntraSite® or Purilon®. After 24 hours, hydrogels of the present invention absorb approximately three times more saline than Purilon and twice that of IntraSite.

Fluid absorption/donation studies were undertaken using the SMTL method as described in Thomas & Hay, 1996, J. Wound Care, 5:3 130–1. The results show that at all concentrations of agar, hydrogels of the present invention consistently absorbed significantly more fluid than Purilon, and did not donate, overall, to any of the concentrations of gelatin used, while Purilon, on the other hand, showed increasing levels of donation up to 45% gelatin.

Increasing agar content raises the overall osmotic potential of the system, thereby representing a progression towards 'drier' wounds. With this progression, the difference between the osmotic potential of the agar gel and the hydrogels is progressively reduced, resulting in progressively lower levels of fluid absorption by both gels. The difference in fluid absorption level between hydrogels of the present invention and Purilon remains essentially constant across all agar concentrations. This a reflection of the constant difference in osmotic potential between hydrogels of the present invention and Purilon, and is a significant advantage of hydrogels of the invention.

In the SMTL method, dry wounds are represented by concentrated gelatin solutions. For all gelatin concentrations, hydrogels of the present invention were found to absorb fluid, indicating that the hydrogels of the present invention generally appear to have a higher osmotic potential than 45% gelatin. It will be appreciated that, by its very nature, a gelatin hydrogel cannot truly represent a dry wound. However, an advantage of the invention is that there is a liquid equilibrium between wound and hydrogel, thus making it possible to deliver drugs and other substances to the wound, even where the overall effect is to absorb exudate, for example.

As a result of the enhanced swelling of the polymer particles, the loss of viscosity of the gel upon dilution with wound fluid is also counteracted. The gel of the present invention is, thus, capable of absorbing more fluid than conventional hydrogels lacking a poloxamer component before the viscosity of the preparation drops to an inadequate value, i.e. before the gel needs replacing.

In general, hydrogels of the present invention may advantageously be used on dry necrotic wounds, such as pressure sores/diabetic wounds, as they can provide moisture to the wound to enhance autolytic debridement; the presence of surfactants is effective in cleansing wounds; and they provide moist wound environment for optimum healing.

In exudating wounds, such as venous/arterial leg ulcers, hydrogels of the present invention provide a significant increase in absorptive capacity and fluid retention; allow reduced maceration of wound and normal tissue; provide for reduced dressing changes and significant cost reductions; and poloxamers have the potential to reduce enzyme related cell damage.

In burns, hydrogels of the present invention control fluid exudates; allow pain reduction; cool wounds through the endothermic process of micellisation; poloxamer gels have been demonstrated to protect cell membranes from damage; can deliver drugs, e.g. Lidocaine.

In infected wounds (e.g. fungating carcinoma), hydrogels of the present invention are advantageous in that: poloxamers have potential anti-bacterial activity, can deliver drugs e.g. Metronidazole; and reduce the effect of odour in these types of wounds.

A particular advantage of the hydrogels of the present invention is that they are capable of holding and dispensing hydrophobic substances, such as hydrophobic drugs, such as vitamins D and E. This has not previously been possible in hydrogels as, by their very nature, they are hydrophilic, and singularly ill-suited to carry or dispense lipophilic or hydrophobic substances. With the present invention, this is now possible and represents a preferred feature thereof.

In acute wounds, such as partial and full-thickness wounds (graft donor sites/grafts and excisions), hydrogels of the present invention can provide a moist wound environment for optimum healing.

The components of the hydrogels of the present invention are generally non-toxic, and safe to use in a wound environment.

Hydrogels of the present invention generally have strong adhesive capabilities. Preferred hydrogels are capable of absorbing at least twice their own weight in exudate.

Certain poloxamers are useful in providing additional benefits, such as in maintaining gel viscosity, gel application and adherence to the wound.

Poloxamers are ABA tri-block co-polymers consisting of polyethylene oxide (PEO) and polypropylene oxide (PPO), and have the general formula

in which 'a' is generally from 2–130 and 'b' is generally from 15–67, although it will be appreciated that other values for 'a' and 'b' are also possible.

Poloxamers are amphiphilic in nature due to the relative hydrophobicity of the central (PO) core and hydrophilicity of the EO end blocks. They are commercially available in varying compositions under the generic name poloxamers [trade names 'Pluronics' (BASF) and 'Synperonics' (ICI)]. The term 'poloxamer' generally applies to any block copolymer of ethylene oxide and propylene oxide which is suitable for use in the present invention, and wherein each 'a' may be the same or different.

Poloxamers affect the adherence of bacteria to a substrate, and provide an anti-bacterial affect by blocking adhesion of bacteria in a wound, for example. In addition, P407, even applied direct to an open lesion, does not gain access to the systemic circulation.

Certain aqueous poloxamer systems exhibit thermally induced viscosification. Such systems are present in a liquid phase at low temperatures but, as the temperature increases, micellisation, followed by gel formation, occurs. Thus, a poloxamer which exhibits "thermally induced viscosification" is one which, at a given concentration in water, tends to form a gel above a given temperature. A system containing such a poloxamer will increase in viscosity with increasing temperature, although the temperature above which gelling occurs, or starts to occur, is dependent not only on the poloxamer, but also on other conditions, such as the nature of any co-solvent.

Poloxamers exhibiting thermally induced viscosification are well known in the art, and are exemplified hereinbelow. For example, aqueous P407, at a concentration of 25% w/v, begins to thicken, or gel, at around 18° C. P407 has the general formula indicated above, in which 'a' is approximately 98 and 'b' is approximately 57.

Known hydrogels decrease in viscosity upon contact with wounds, owing to the increase in temperature. This is a significant disadvantage of such gels, as the decrease in viscosity of the gel provides similar problems to those of gel dilution. Where this could be a problem, then it is advantageous to employ poloxamer systems which exhibit thermally induced viscosification. A hydrogel comprising such a poloxamer system, comprising one or more poloxamer components which gel at temperatures somewhere between ambient and 35° C., increases in viscosity upon application to a wound, thereby facilitating both application of the gel to the wound and helping to maintain gel integrity on the wound. It will be appreciated that preferred gels of the present invention are already viscous prior to application, and that the viscosity increases in the above circumstances.

Any poloxamer capable of causing polymer particle swelling is suitable for use in the present invention. In general suitable poloxamers are those which readily dissolve in water, at least to 10% w/v. In addition, combinations of poloxamers may be employed, such as a combination of P188 and P407, for example. Such combinations, especially of structurally dissimilar poloxamers, have advantageous solubilising effects.

More preferred are poloxamers which, in aqueous solution, are capable of forming a weak gel upon heating, to provide the advantages of increased viscosity and adherence to the wound. A weak gel is a term of art, as defined in, for example, Ross-Murphy "Physical techniques for the study of food biopolymers", (1994) Blackie Academic and Professional. From the commercially available range, available from BASF and UniQuema for example, suitable poloxamers are F127, F108, F88, F87, P188 and F98. Poloxamers F127, F108, F88 and F87, also referred to as P407, P338, P238 and P237 respectively herein, are more preferred, and fall into the category of being able to form weak gels, on heating.

The gelling characteristics of the poloxamer system may suitably be so selected as to gel and to increase in viscosity at wound temperature. It will be appreciated that such a system includes the cross-linked polysaccharide, water and any co-solvent, as well as any other components, such as pharmaceuticals, enzymes, thickeners and the like. In general, the properties of poloxamers are little affected by other components in the system. Cross-linked polysaccharides gel water at low concentrations, but the gelling effect, where present, of the poloxamer is still present and largely unaffected by either the polysaccharide or any ionic components.

Some of the preferred poloxamers of the present invention have the following characteristics:

Poloxamer P 407 (F 127)
Approximate molecular weight—12,000 Daltons
Approximate molecular weight of PPO block—3,600 Daltons
Approximate weight of PEO blocks—4,200 Daltons (each terminal block)
Approximate structure $(EO)98(PO)57(EO)98$ Poloxamer P 237 (F87)
Approximate molecular weight 14,000 Daltons
Approximate molecular weight of PPO block 3,250 Daltons
Approximate weight of PEO blocks 5,400 for each terminal block
Approximate structure $(EO)112(PO)56(EO)112$ Poloxamer P 338 (F 108)
Approximate molecular weight 7,700 Daltons
Approximate molecular weight of PPO block 2,250 Daltons
Approximate weight of PEO blocks 2,700 for each terminal block
Approximate structure $(EO)78(PO)40(EO)78$ Poloxamer P 188 (F 68)
Approximate molecular weight 8,350 Daltons
Approximate molecular weight of PPO block 1,750 Daltons
Approximate weight of PEO blocks 3,300 for each terminal block
Approximate structure $(EO)60(PO)30(EO)60$ Details concerning the approximate molecular weight and composition of a wide range of poloxamers can be found in Paterson et al., 'Handbook of engineering polymeric materials', (1997) pp. 765ff.

Where a single poloxamer is used in accordance with the present invention, this is most preferably P407, but any of the poloxamers which form weak gels upon heating to body temperature can be utilised for providing thermogelling characteristics to the gel. Combinations with other poloxamers may also be beneficial in modifying the rheology of the gel system, for example, to provide desirable characteristics. For example, P407 in combination with P188 allows the gelling properties of P407 to be modified, and such modification is readily within the art of the skilled person.

Suitably, the concentration of the poloxamer component is between 5% w/w of the hydrogel and 30% w/w, with 10% to 25%, and 10 to 20% being more preferred. A preferred figure for P407, especially, is 14% w/w. It will be appreciated that the concentration of poloxamer will depend on the poloxamer(s) and the effect it is desired to achieve, and that determination of suitable concentrations is within the skill of those in the art. However, regardless of the nature of the composition, the maximum concentration may depend, for example, on the ability to mix the formulation on the one hand (viscosity), and the requirement to maintain the temperature of any viscosity increase at a point in between ambient and wound temperature. Some preparations may already have gelled at ambient temperature, and be prepared at low temperatures, and these form an embodiment of the present invention. This balance may be readily assessed by the skilled practitioner.

It will be appreciated that the amount of poloxamer may be varied as desired. Although it is possible to have concentrations of poloxamer up to 25%, or even higher, there is generally little need for such preparations in accordance with the present invention, and suitable concentrations will typically range from about 10% to about 18%, with concentrations of about 11% to about 16% generally being preferred.

Suitably, the gel of the present invention additionally comprises an optional co-solvent, preferably propylene glycol. This solvent is suitably incorporated at a concentration of about 20%, although values of between 10 and 30%, preferably 15 and 25%, may also be used, as appropriate, or as desired. The exact amount of co-solvent will depend on what is required, such as any effect upon the type of poloxamer that is used, and may be readily determined by the skilled person. Concentrations below 10% generally exhibit little useful effect, while concentrations above 30% are more expensive, and exhibit little more effect than lower concentrations.

Propylene glycol can also exhibit an effect on gelling temperatures. For example, 16% w/w P407 gels at 27° C. in water and at 23° C. in 20% aqueous propylene glycol solution. Propylene glycol, then, generally has two advantages. The first lies in its antimicrobial properties, while the second is its ability to act as co-solvent and modifier for poloxamer. It will be appreciated that the present invention, where it is desired to use either bacteriostats/cides and/or co-solvents, envisages other suitable compounds, as are well known in the art.

Suitable co-solvents, for example, should be pharmaceutically acceptable in the context of the relevant preparation. Determination of the pharmaceutical acceptability of any particular co-solvent is within the skill of those in the art. Suitable co-solvents will be readily apparent to those skilled in the art, and should be compatible with an aqueous solution of the poloxamer and should not separate out from a preparation if the preparation is allowed to stand at ambient temperature. A particularly suitable co-solvent is propylene glycol, but other co-solvents will be apparent to those skilled in the art, and are preferably chemically similar to propylene glycol.

In the context of bacteriostasis, it is preferred that propylene glycol should be used in concentrations of no less than about 10%. In general, it is preferred to use propylene glycol in concentrations of from about 15% to 25%, preferably 15% to about 20% and more preferably, in the region of 20%.

It will also be appreciated that further substances may be added to the preparation to modify the rheological properties of the preparation, and these may comprise alcohols and/or humectants, for example, provided that they are pharmaceutically or therapeutically acceptable.

In general, suitable ranges for components of the hydrogels of the present invention are as follows:

| | |
|---|---|
| Cross-linked sodium carboxymethylcellulose | 1–2.5% w/w |
| Poloxamers | 5–25% w/w |
| Propylene Glycol | 10–20% w/w |
| Water | 52.5%–84% w/w |

Hydrogels located at the lower end of the above ranges for cross-linked CMC and poloxamer are generally suitable where slightly more fluid gels are acceptable and where increased fluid donation properties are required.

The gel of the present invention may also be used with suitable medicaments for wound treatment. As such the invention extends to compositions as previously defined, additionally comprising a medicament. Suitable medicaments include the general classes of:

1) Antibacterial agents, such as metronidazole, silver;
2) Anaesthetic/analgesics, such as lidocaine, benzovaine;
3) Anti-inflammatory agents, such as steroidal, non-steroidal;
4) Growth factors, such as transforming growth factor beta, endothelial growth factor, basic fibroblast growth factor, nerve growth factor;
5) Autologous cells, such as epithelial cells, fibroblasts;
6) Cellular matrix components, such as collagen, hyaluronic acid;
7) Enzymes for debridement, such as subtilysin, bromain, papain; and
8) Genes for gene therapy, such as the vascular endothelial GF-2 (VEGF) angiogenesis gene.

It will be appreciated that the above list, while representing preferred hydrogels additives, are illustrative, and non-limiting. It will be appreciated that other suitable compounds may be used, as appropriate.

Thus, it will be appreciated that hydrogels of the present invention may be used to deliver both hydrophobic and hydrophilic drugs topically.

Hydrogels of the present invention may also be used as an implantation delivery system. They may also be used in slow release delivery devices for drugs such as lidocaine (for pain control) and metronidazole (for fungating wounds) in topical wound care applications; as well as in association with growth factors, such as EGF, FGF, PDGF and VEGF, for wound care applications.

Hydrogels of the present invention may also be used for the delivery of autologous cells such as fibroblasts and keratinocytes and for the delivery of skin matrix protein, such as collagen or hyaluronic acid; and/or for providing a delivery system for enzymes used to debride necrotic and sloughy wound tissue.

Hydrogels of the present invention containing metronidazole, for example, may be used in the treatment of malodorous wounds, and are more effective against aerobic pathogenic organisms, such as *Staphylococcus aureus*, *Escherichia coli* and *Pseudomonas aeruginosa*, than medicated type tulle dressings containing metronidazole.

Tissue-repairing agents useful in the present invention include a number of growth factors, including epidermal growth factor (EDF), PDGF, and nerve growth factors (NGF's). Generally, growth-promoting hormones will affect between one and four tissues. Many of the products developed from such proteins are targeted towards wound repairs of one kind or another, although there are other indications. Some of the most important tissue growth factors are described further below.

Epidermal Growth Factor (EGF) was discovered after the observation that cutaneous wounds in laboratory mice seemed to heal more rapidly when the mice were allowed to lick them. This was not simply due to some antiseptic agent in saliva (such as lysozyme). A specific growth factor, now known as EGF, was shown to be responsible. EGF is identical to urogastrone, and has angiogenic properties. Transforming growth factor-alpha (TGF-α) is very similar, binding to the same receptor and is even more effective in stimulating epithelial cell regeneration (epithelisation).

Thus, hydrogels of the present invention comprising EGF/TGF may advantageously be used in the acceleration of wound healing and burns, reduction in keloid scar formation (especially for burns), skin engraftment dressings, and the treatment of chronic leg ulcers.

A further area is in ophthalmology in treating corneal injuries, which often heal slowly and imperfectly because of the minimal oxygenation of the corneal epithelium. The cornea has no blood supply, so the corneal cells obtain their oxygen from ambient air. Because corneal lesions heal so slowly, scar tissue formation is often excessive and this impairs vision. Scarring can be reduced by using EGF topically. Eye operations, e.g. for cataract removal or corneal transplantation, should also be healed more rapidly if EGF is used, although prolonged application might cause eye pain. It will be appreciated that hydrogels may only be used in such circumstances if the lids can be prevented from closing and removing the gel.

In common with other naturally occurring compounds, EGF may be provided in more than one form, and the present invention encompasses any such derivatives and variants, as well as pro-drugs, of compounds useful to be delivered by the hydrogels of the present invention. Derivatives may be chemically synthesised, for example, such as by taking the parent molecule and derivatising it, or by preparing the molecule by an alternative synthetic route. Variants may be those which occur naturally, or which may be engineered, such as by alteration of a nucleotide sequence encoding a protein, or by preventing or altering post-synthetic processing, for example. In the case of EGF, DWP401 is a recombinant human version, produced by Daewoong, and is a potent stimulator of epithelial cell proliferation. Pro-drugs are generally inactive forms of the drug which activate at the situs, or forms which have been engineered for ease of delivery, for example. In any event, a pro-drug is metabolised or otherwise converted to the parent drug prior to, or at the site of, action.

Platelet-Derived Growth Factor (PDGF) is a mitogen for almost all mesenchymally-derived cells, i.e. blood, muscle, bone, cartilage, and connective tissue cells. It is a dimeric glycoprotein existing as AA or BB homodimers, or as the AB heterodimer. As with many growth factors, PDGF is now considered to be a member of a larger family of factors. In addition to PDGF, this family includes the homodimeric factors vascular endothelial growth factor (VEGF) and placental growth factor (PIGF), VEGF/PIGF heterodimers, and connective tissue growth factor (CTGF), a PDGF-like factor secreted by human vascular endothelial cells and fibroblasts. Along with NGF, TGF-β and glycoprotein hormones such as human chorionic gonadotropic hormone (hCG), PDGF is now classified as a member of the cysteine-knot growth factor superfamily. All of these factors may be used in conjunction with hydrogels of the present invention.

PDGF is produced by platelets and released in the course of blood clotting. It is just one of the growth factors that derive from these cells. PDGF attracts fibroblasts and white blood cells to the site of the injury, as well as stimulating the growth of replacement connective tissue (mainly fibroblasts and smooth muscle cells). It stimulates cell division in various cells, including those that produce collagen, so encouraging angiogenesis. It also stimulates mitogenesis, vasoconstriction, chemotaxis, enzyme activity and calcium mobilisation;

Blood platelet derived growth factors may be used to restore bone and soft tissue regrowth during dental and orthopaedic treatments and to accelerate the healing process of chronic and acute wounds. Accordingly, hydrogels of the present invention may advantageously comprise a platelet derived growth factor cocktail.

Hydrogels of the present invention may be used in gene therapy for local delivery of the PDGF gene, for example. Plasmid DNA encoding PDGF is incorporated into the hydrogel matrix and granulation tissue fibroblasts, which originate in viable tissue surrounding the wound, proliferate and migrate into the matrix, acting as targets for plasmid gene transfer and expression.

Vascular Endothelial Growth Factor (VEGF—also known as vascular permeability factor) is another vascular growth factor, and is a multifunctional angiogenic cytokine. It contributes to angiogenesis (blood vessel growth) both indirectly and directly by stimulating proliferation of endothelial cells at the microvessel level, causing them to migrate and to alter their generic expression. VEGF also makes theses endothelial cells hyperpermeable, causing them to release plasma proteins outside the vascular space, which causes changes in the area, contributing to angiogenesis.

Fibroblast Growth Factor (FGF) is actually a family of at least 19 14–18 kD peptides belonging to the heparin-binding growth factors family, and are mitogenic for cultured fibroblasts and vascular endothelial cells. They are also angiogenic in vivo and this angiogenicity is enhanced by TNF. FGF's may be used in a similar manner to EGF. bFGF, also known as FGF-2, is involved in controlling human megakaryocytopoiesis and FGFs have been shown to be effective in stimulating endothelial cell formation, and in assisting in connective tissue repair.

Hydrogels comprising Keratinocyte Growth Factor (KGF), also known as FGF-7, may be used in wound healing and other disorders involving epithelial cell destruction.

Transforming Growth Factors (TGF's) have the ability to transform various cell lines, and can confer, for example, the ability to grow in culture for more than a limited number of generations, growth in multiple layers rather than monolayers, and the acquisition of an abnormal karyotype. There are at least five members of the TGF family, the two most widely studied being TGF-α and TGF-β. The former is mitogenic for fibroblasts and endothelial cells, angiogenic, and promotes bone resorption.

TGF-β is a general mediator of cell regulation, a powerful inhibitor of cell growth, and inhibits the proliferation of many cell types. TGF-β can antagonise the mitogenic effects of other peptide growth factors, and can also inhibit the growth of many tumour cell lines. TGF-β also has angiogenic effects, and promotes collagen formation in fibroblasts. Indications for hydrogels of the present invention include chronic skin ulcers, such as neurotrophic foot ulcers in diabetic patients. Other areas include wound healing, bone repair and immunosuppressive diseases.

A recent advancement in wound management is Tissue Engineering (TE). TE and related developments help growth of tissue, as well as relieving pain and suffering for thousands of patients otherwise left without an adequate treatment alternative. TE is applicable, particularly for chronic wounds, but also for burns and, increasingly, cosmetic and plastic surgery where the rapid surge in such procedures has concomitantly led to rising numbers of patients presenting complications, such as laser burns.

Hydrogels of the present invention may be used to carry suitable cells, for example. These may be incorporated into the gel just prior to application to a wound, or other suitable area, to maximise efficacy. Suitable cells include autologous fibroblasts and keratinocytes, which are mainly responsible for dermis and epidermis formation. Separate gels each comprising one cell type may be applied consecutively or together, or one gel may comprise both cell types, but this is generally less preferred.

Hydrogels of the present invention may usefully comprise collagen, for example. Although collagen, in this form, is unlikely to serve a useful structural function, it primarily serves as a sacrificial protein where proteolytic activity is undesirably high, thereby helping to prevent maceration of healthy tissue, for example.

Enzymes are used in the debridement of both acute and chronic wounds. Debridement is the removal of nonviable tissue and foreign matter from a wound and is a naturally occurring event in the wound-repair process. During the inflammatory phase, neutrophils and macrophages digest and remove "used" platelets, cellular debris, and avascular injured tissue from the wound area. However, with the accumulation of significant amounts of damaged tissue, this natural process becomes overwhelmed and insufficient. Build-up of necrotic tissue then places considerable phagocytic demand on the wound and retards wound healing. Consequently, debridement of necrotic tissue is a particular objective of topical therapy and an important component of optimal wound management.

It will be appreciated that debridement reduces the bioburden of the wound. Because devitalised tissue supports the growth of bacteria, the presence of necrotic tissue places the patient at risk for wound infection and sepsis. Using external measures to remove the necrotic tissue and foreign matter reduces the volume of pathogenic microbes present in the wound. It controls and potentially prevents wound infections, particularly in the deteriorating wound. Debridement also facilitates visualisation of the wound wall and base. At a molecular level, debridement interrupts the cycle of the chronic wound so that protease and cytokine levels more closely approximate those of the acute wound.

Autolysis is the lysis of necrotic tissue by the body's white blood cells and enzymes, which enter the wound site during the normal inflammatory process. Proteolytic, fibrinolytic, and collagenolytic enzymes are released to digest the devitalised tissue present in the wound. Autolysis is a selective method of debridement that leaves healthy tissue intact. Autolysis, a naturally occurring physiologic process, occurs in the presence of a moist, vascular environment. The primary requirements for debridement via autolysis include a moist wound environment, adequate leukocyte function, and an adequate neutrophil count. Autolysis is enhanced or supported by applying a moisture-retentive dressing to the necrotic wound and allowing it to remain undisturbed for a reasonable length of time. By maintaining a moist wound environment, the cellular structures that are essential for phagocytosis (neutrophils and macrophages) remain intact and are not prematurely destroyed through desiccation. Since an important role of macrophages is to produce growth factors, the presence of healthy macrophages in the wound fluid supports the continued production of growth factors.

Autolysis is encouraged by hydrogels of the present invention, even when they contain no active debridement ingredients. This can be used alone or in combination with other debridement techniques. However autolysis as a sole method of debridement is only recommended for non-infected wounds with a limited volume of necrotic tissue. It is desirable to promote autolysis in all debridement modalities so that cellular desiccation through air exposure and the resulting build-up of necrotic tissue are avoided. For example, after surgical sharp debridement of a pressure ulcer, the application of a hydrogel-impregnated gauze can maintain a moist wound environment, thus preventing tissue desiccation and promoting continued softening and loosening of residual necrotic tissue.

Autolysis is generally slower than other debridement methods, and the time frame for autolysis to occur varies depending on the size of the wound and the amount and type of necrotic tissue. Initially, the black eschar will loosen from the edges, become soft, change to brown or grey in colour, and eventually transform into stringy yellow slough. It is desirable to monitor the wound closely during the autolysis process because as the wound debrides, the full wound bed and walls are exposed and the true extent of the wound is revealed. Consequently, the wound will increase in length, width and depth necessitating a change in the therapy.

Debridement by autolysis compares favourably with other methods of debridement in terms of effectiveness. Peri-wound maceration can develop when wound exudate has continued contact with intact skin. The potential for maceration is increased in the more exudative wound, such as the infected wound or a venous ulcer. Liquid barrier film or skin barriers are advantageously applied to the surrounding skin, in such circumstances, as prophylaxis. It is desirable to select and change dressings at appropriate intervals so as to manage exudate levels and reduce the likelihood of maceration of the peri-wound skin.

Wounds can also be debrided chemically with the use of enzymes, or sodium hypochlorite (Dakin's solution), for example. These methods remove the necrotic tissue through a chemical process (chemical debridement).

Enzymes, for example, may be incorporated into hydrogels of the present invention for topical application to provide a selective method of debridement. Suitable enzymes may be derived from various sources, such as krill, crab, papaya, bovine extract, and bacteria Commercially available, suitable enzymes include collagenase, papain/urea, and a fibrinolysin and deoxyribonuclease combination.

Enzymes for use in the present invention generally work in one of two ways: by directly digesting the components of slough (e.g., fibrin, bacteria, leukocytes, cell debris, serous exudate, DNA); or, by dissolving the collagen "anchors" that secure the avascular tissue to the underlying wound bed.

Collagenase-containing hydrogels of the present invention may be used to treat dermal pressure ulcers and burn wounds, for example. Other indications for hydrogels comprising collagenase include Peyronie's disease, Dupuytren's contracture, keloids, and nerve healing.

Hydrogels of the present invention may comprise Dakin's solution, if desired, generally to exert antimicrobial effects and odour control. As a debridement agent, Dakin's solution is non-selective because of its cytotoxic properties. Dakin's solution denatures protein, rendering it more easily removed from the wound. Loosening of the slough also facilitates debridement by other methods. Hydrogels comprising Dakin's solution may be changed twice daily if the goal is debridement. Periwound skin protection should generally be provided with ointments, liquid skin barrier film dressings, or solid skin barrier wafers, for example.

Hydrogels of the present invention may also be used to treat fistulae. The hydrogel can easily be squeezed into the wound, and its three dimensional structure and its ability to absorb water enable it to support wound drainage. Additionally its bacteriostatic properties and hydrolytic and cleansing activity debride both necrosis and slough.

The present invention also extends to a method for the preparation of a gel, comprising the steps of: mixing a cross-linked polysaccharide (such as CMC) and poloxamer in a solvent (such as propylene glycol) to form a slurry, water being added with continual stirring, and removing entrapped air, such as by centrifugation. Details of suitable methods of gel preparation are given in Examples 1 and 2.

The gel of the present invention may be delivered by any suitable method, such as via a syringe or bellows pack (single dose delivery systems) or a multidose system, such as a pressurised delivery system or delivery via a 'bag in the can' type system (such as that published in WO98/32675). An example of a bellows pack is shown in published UK design number 2082665.

As such, the present invention also extends to a single dose delivery system comprising a gel according to the present invention, for the treatment of wounds. The invention also extends to a pressurised delivery system comprising a gel according to the present invention, and a pressurised hydrogel according to the present invention in an aerosol container capable of forming a spray upon release of pressure therefrom.

Use of such delivery means allows the gel to be delivered to areas on a patient which are otherwise difficult to reach by direct application, such as on the back of a patient when the patient is lying down. The poloxamer component in combination with the cross-linked polysaccharide absorbent component then allows the gel to set in this position, even when gravity would tend to act on the gel to remove it from the wound.

In one method of production, both the poloxamer and the carboxymethylcellulose are slurried together in propylene glycol prior to adding the water. Mixing may then be effected at high velocity. Any resulting air bubbles may be removed, such as by centrifugation. Typical viscosity of the resulting gel is at r.t.p. is approximately 400 Pa·s. For large scale preparation, reduction in air bubbles may be effected by conducting the process under a vacuum, for example, and generally minimising any process feature likely to introduce bubbles, which may present a particular problem, as poloxamers are surfactants. This may be achieved by reducing unnecessary head space above the rotor and, more particularly, ensuring that the rotor does not clear the mix, if possible. Degassing components of the formulation prior to mixing is also particularly desirable.

When hydrogels of the present invention comprise further ingredients, such as enzymes or proteins, then suitable amounts of such ingredients will be readily apparent to those skilled in the art. For example, amounts of enzymes will depend on the purpose they are to perform, and the extent to which they are required. Amounts of 0.5% to 3% w/w are generally suitable for enzymes, while amounts of about 0.01% to about 1% are generally suitable for hormones. In addition, as with any labile substance, it may be desirable to incorporate a stabiliser for a delicate biological, for example, such as an enzyme, in order that the substance not break down unduly prior to reaching the site of action. Such stabilisers will vary from substance to substance, and are readily apparent to those skilled in the art.

Collagen and hyaluronic acid may be present in amounts of about 1% to about 10% w/v, as desired.

When hydrogels are used as cell matrices, then cells may be present in amounts of about 1% to about 10% by volume. Dakin's solution may substantially replace water in the hydrogel, and has little effect on the poloxamer component.

It is an advantage of the present invention that the properties, such as gelling, of the poloxamer(s), are largely independent of the amount of cross-linked polysaccharide present, thus making the properties of any hydrogel more easy to predict, particularly in the region of 25–30° C.

Hydrogels of the present invention may be sterilised by autoclaving, or by using sterile components in a sterile environment, for example. Autoclaving at 121° C. for 15 minutes works well. Gamma irradiation and electron beam irradiation tend to denature the hydrogel, and are not recommended.

Preferred hydrogels for use on wounds, for example, comprise a poloxamer component which gels at a temperature in the region between ambient and of that of the body/wound temperature (25° C.–35° C.), and are generally stable up to 40° C.

Hydrogels of the present invention are substantially non-toxic. This is not surprising, as the components are preferably selected from non-toxic ingredients.

In a preliminary case study, a horse presented with a deep chest wound caused by a road traffic accident. The wound had initially been treated by surgical debridement of damaged tissue followed by suturing of the remaining healthy tissue. Subsequently, due to infection and oedema, the wound failed to heal, and the remaining sutures had to be removed, leaving a large exudating wound with areas of black necrotic tissue, sloughy tissue exhibiting infection, and healthy areas undergoing re-epithelisation.

The hydrogel of Example 1 was applied directly to the surface of this wound at 24 hour intervals with no secondary dressing. At intervals of 24 hours the wounds were irrigated with tap water and hydrogel re-applied (photographs and subjective evaluations of wound were undertaken at these time points).

Within 24–48 hours the majority of the necrotic wound tissue had been debrided, leaving healthy tissue. Tissue that had demonstrated areas of re-epithelisation showed excellent rates of healing above what had been expected, and wound infection had also been significantly reduced.

In summary the debridement and healing effects of hydrogels of the present invention were significantly greater than had been seen with other types of amorphous hydrogels that veterinary clinicians had previously used.

Drugs and any other loading substances, such as enzymes, may be loaded at any stage desired. With thermolabile substances, this is preferably after sterilisation, where this is by autoclaving, and may be effected immediately prior to administration. Where the substance is stable, this may be added to any phase during preparation, but it is generally preferable to add the substance to the poloxamer, prior to adding the poloxamer. Where the poloxamer gels, then it is preferable to add the substance to a liquid phase of the poloxamer, either at a low temperature below gelling, or at a temperature above gelling, where the poloxamer has re-liquified.

It is an advantage of the present invention that poloxamers are capable of releasing proteins, for example at zero order rates. Thus, hydrogels of the present invention are useful in delivering substances in a sustained release manner. Preferred substances are proteins, such as enzymes, but other substances are also deliverable in such a fashion. Thus, the hydrogels of the present invention, in a preferred embodiment, form sustained release vehicles for substances desired to be delivered to skin or a skin lesion, such as a wound.

Hydrogels of the present invention are also useful in the treatment of cancerous skin lesions, as poloxamers are effective in overcoming multi-drug resistance in cancer cells. Essentially it has been shown that Pluronics "hypersensitise" multiple drug resistant cancer cells resulting in an increase of the cytotoxic activity of anti-neoplastic agents with respect to these cells by two to three orders of magnitude.

The present invention will now be illustrated by the following examples, which are illustrative of, but not binding upon, the present invention.

EXAMPLE 1

Preparation of Wound Gel

The following represents the production of a 116 g batch of product:

Slurry 2 g of Aquasorb A380 in 20 g of propylene glycol by mixing for 10 minutes with overhead stirrer at 1000 rpm. Add 16 g of poloxamer P407 and continue mixing for a further 10 minutes with overhead stirrer at 1000 rpm. Add 78 g of distilled water and mix for a further 2 hours with an overhead stirrer at 1000–1200 rpm, whilst maintaining the sample at a temperature of less than 15° C. Remove sample to centrifuge tubes and centrifuge at 4000 rpm for 2 hours.

By w/w, the thus obtained formulation equates to 1.7%, 13.8%, 17.2% and 67.3% of the cross-linked CMC, poloxamer 407, propylene glycol and water respectively.

EXAMPLE 2

Preparation of Wound Gel

Following a similar procedure to that of Example 1, but reducing head space, de-gassing the components and mixing under vacuum, a wound gel having the following formulation was prepared:

| | |
|---|---|
| Cross-linked sodium carboxymethylcellulose | 2.0% w/w |
| Poloxamer 407 | 14.5% w/w |
| Propylene Glycol | 20% w/w |
| Water | 63.5% w/w |

The above process involved the following steps:

1) pre-dissolving the poloxamer in the water and leaving overnight at reduced temperatures (<12° C.) to defoam;
2) slurrying the Aquasorb in the majority of the propylene glycol and adding to the vessel under pressure via an in-line homogeniser; and
3) Optimising agitation so as to a) ensure the prevention of sedimentation of the Aquasorb component and b) not to be so vigorous that either the mixer blades or the displaced mixture breaks the surface, leading to foam formation and air entrapment.

No vacuum was used in this process. The process took four hours for a 600 Kg batch.

EXAMPLE 3

Preparation of Gel Containing Poloxamer 338

A 116 g batch of product is prepared as follows:

Slurry 2 g of Aquasorb A380 in 20 g of propylene glycol by mixing for 10 minutes with overhead stirrer at 1000 rpm. Add 20 g of poloxamer P338 and continue mixing for a further 10 minutes with overhead stirrer at 1000 rpm. Add 74 g of distilled water and mix for a further 2 hours with an overhead stirrer at 1000–1200 rpm, whilst maintaining the sample at a temperature of less than 15° C., but above freezing. Remove sample to centrifuge tubes and centrifuge at 4000 rpm for 2 hours.

By w/w, the thus obtained formulation equates to 1.7%, 17.2%, 17.2%, and 63.8% of the cross-linked CMC, poloxamer 338, propylene glycol and water respectively.

EXAMPLE 4

Enhanced Swelling of Cross-linked Polymer Particles in the Presence of Poloxamer Molecules The hydrodynamic diameter of the cross-linked CMC particles in the absence and presence of poloxamer P407 was determined by laser diffraction using a Malvern Instruments Mastersizer 2000.

0.2% and 0.5% w/w dispersions of Aquasorb™ A380 (Honeywell & Stein, Times House, Throwley Way, Sutton, UK) were prepared in distilled water, and 16% w/w aqueous P407 solution by means of overhead siring for a period of 30 minutes. Aliquots of each sample were then dispersed into the circulating fluid (distilled water) of the Mastersizer instrument and the particle size distribution of the Aquasorb particles determined. Each sample was analysed in triplicate. The median diameter of the Aquasorb particles from the various dispersions is tabulated beneath. It can be seen that for both starting concentrations, the median diameter of the Aquasorb particles was significantly greater in the presence of the poloxamer molecules.

| [Aquasorb]/% w/w | No Poloxamer | +16% w/w P 407 |
|---|---|---|
| 0.2 | 220 μm | 310 μm |
| 0.5 | 215 μm | 280 μm |

EXAMPLE 5

Interpenetration of Poloxamer and Polymer Particles

Figure 2:
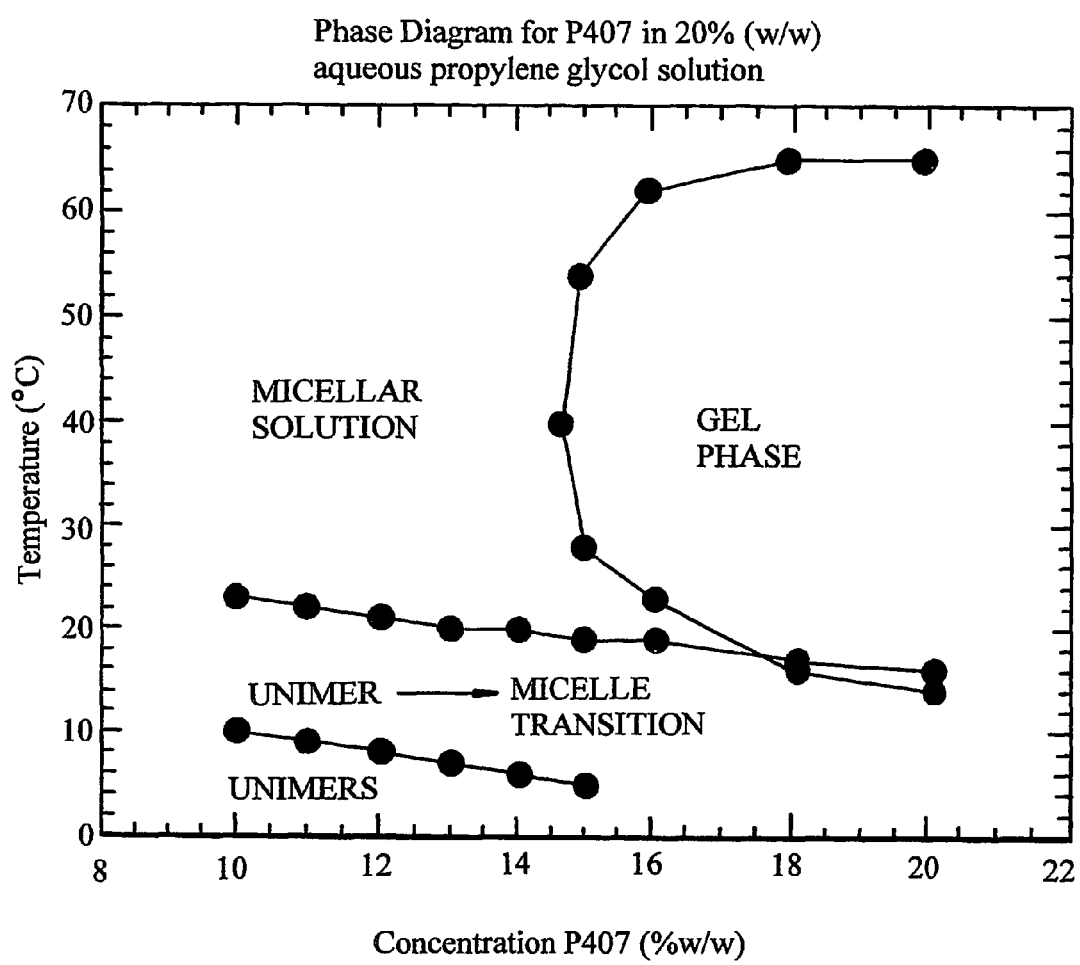
FIG. 2 is the phase diagram of poloxamer P407 in 20%(w/w) aqueous propylene glycol.

The viscosity-temperature profile of the formulation as described in Example 1 displays an increase in viscosity at a temperature of approximately 27° C. (FIG. 1). Cross reference with the phase diagram of poloxamer P407 in 20% w/w aqueous propylene glycol (FIG. 2) indicates that such thermorheological behaviour is indicative of a concentration of P 407 in the solvent phase of the mixed system of approximately 15.3% w/w. Consequently, through comparison with the composition of the formulation (Example 1) it can be inferred that the poloxamer molecules have access to approximately 90% of the solvent phase.

EXAMPLE 6

Effect of Added Poloxamer on the Size of Cross-Linked CMC Particles

Two grades of cross-linked CMC were used—Aquasorb A380 and Aquasorb A500, both from Honeywell and Stein. The poloxamers used were P237, P338 and P407, from BASF.

Samples were prepared in distilled water containing either 0.2 or 0.5% w/w cross-linked CMC (either Aquasorb A 380 or Aquasorb A 500) and either 0, 5, 10 or 15% W/w of either Poloxamer P237, P338 or P407. All samples were made up according to the following protocol 1. Add CMC
2. Add Poloxamer
3. Add water Following addition of all components, the samples were left to tumble for ~24 hours at ambient temperature. After this time, all samples were clear and the poloxamer and CMC were fully dissolved.

All particle size analyses were performed on a Mastersizer 2000 Laser Diffraction System (Malvern Instruments). A background solvent (aqueous phase) was circulated continuously in a closed circuit through the sample cell. Small amounts of sample (5 to 10 ml) were sequentially added to the aqueous phase until an obscuration reading greater than 5 was obtained. The size of the swollen CMC particles was recorded in terms of their d(0.5) value. This parameter represents the value at which 50% of the particles within the sample have a larger diameter and similarly 50% of the particles have a sample diameter.

The values of d(0.5) obtained for the various CMC/Poloxamer combinations are given in the Tables beneath.

| Aquasorb A 380/Poloxamer P 237 | | |
|---|---|---|
| [CMC]/% w/w | [Poloxamer]/% w/w | d(0.5)/μm |
| 0.2 | 0 | 220 |
| 0.2 | 5 | 304 |
| 0.2 | 10 | 312 |
| 0.2 | 15 | 329 |
| 0.5 | 0 | 230 |
| 0.5 | 5 | 318 |
| 0.5 | 10 | 331 |
| 0.5 | 15 | 338 |

| Aquasorb A 500/Poloxamer P 237 | | |
|---|---|---|
| [CMC]/% w/w | [Poloxamer]/% w/w | d(0.5)/μm |
| 0.2 | 0 | 220 |
| 0.2 | 5 | 334 |
| 0.2 | 10 | 351 |
| 0.2 | 15 | 353 |
| 0.5 | 0 | 200 |
| 0.5 | 5 | 333 |
| 0.5 | 10 | 342 |
| 0.5 | 15 | 357 |

| Aquasorb A 380/Poloxamer P 338 | | |
|---|---|---|
| [CMC]/% w/w | [Poloxamer]/% w/w | d(0.5)/μm |
| 0.2 | 0 | 220 |
| 0.2 | 5 | 310 |
| 0.2 | 10 | 319 |
| 0.2 | 15 | 334 |
| 0.5 | 0 | 230 |
| 0.5 | 5 | 300 |
| 0.5 | 10 | 312 |
| 0.5 | 15 | 331 |

| Aquasorb A 500/Poloxamer P 338 | | |
|---|---|---|
| [CMC]/% w/w | [Poloxamer]/% w/w | d(0.5)/μm |
| 0.2 | 0 | 220 |
| 0.2 | 5 | 328 |
| 0.2 | 10 | 338 |
| 0.2 | 15 | 347 |
| 0.5 | 0 | 200 |
| 0.5 | 5 | 347 |
| 0.5 | 10 | 347 |
| 0.5 | 15 | 352 |

| Aquasorb A 380/Poloxamer P 407 | | |
|---|---|---|
| [CMC]/% w/w | [Poloxamer]/% w/w | d(0.5)/μm |
| 0.2 | 0 | 220 |
| 0.2 | 0.1 | 256 |
| 0.2 | 1 | 287 |
| 0.2 | 5 | 309 |
| 0.2 | 10 | 314 |
| 0.2 | 15 | 317 |
| 0.5 | 0 | 230 |
| 0.5 | 5 | 306 |
| 0.5 | 10 | 321 |
| 0.5 | 15 | 334 |

| Aquasorb A 500/Poloxamer P 407 | | |
|---|---|---|
| [CMC]/% w/w | [Poloxamer]/% w/w | d(0.5)/μm |
| 0.2 | 0 | 220 |
| 0.2 | 5 | 322 |
| 0.2 | 10 | 339 |
| 0.2 | 15 | 352 |
| 0.5 | 0 | 200 |
| 0.5 | 5 | 328 |
| 0.5 | 10 | 332 |
| 0.5 | 15 | 357 |

From the above Tables, it can be seen that, for all of the CMC/Poloxamer combinations studied, there is an approximate 50% increase in the value of d(0.5) for the CMC particles, following prolonged contact (~18 hours) with 5–15% w/w poloxamer solutions, compared to the value obtained for the CMC particles in distilled water. It can also be seen that there is a general progressive increase in particle size for any CMC/Poloxamer concentration upon increasing the concentration of poloxamer from 5 to 15% w/w.

EXAMPLE 7

Preparation of Wound Gel Containing Metronidazole (Anti-Bacterial Agent)

A 116 g batch of product is prepared as follows:

Slurry 2 g of Aquasorb A380 in 20 g of propylene glycol by mixing for 10 minutes with overhead stirrer at 1000 rpm. Add 16 g of poloxamer P407 and continue mixing for a further 10 minutes with overhead stirrer at 1000 rpm. Dissolve 1.1 g of metronidazole hydrochloride in 76.9 g of distilled water, then add to the Aquasorb A 380/propylene glycol slurry and mix for a further 2 hours with an overhead stirrer at 1000–1200 rpm, whilst maintaining the sample at a temperature of less than 15° C. Remove sample to centrifuge tubes and centrifuge at 4000 rpm for 2 hours.

By w/w, the thus obtained formulation equates to 1.7%, 13.8%, 17.2%, 0.8% and 66.3% of the cross-linked CMC, poloxamer 407, propylene glycol, metronidazole and water respectively.

EXAMPLE 8

Preparation of Wound Gel Containing Lidocaine (Local Anaesthetic)

A 116 g batch of product is prepared as follows:

Slurry 2 g of Aquasorb A380 in 20 g of propylene glycol by mixing for 10 minutes with overhead stirrer at 1000 rpm. Add 16 g of poloxamer P407 and continue mixing for a further 10 minutes with overhead stirrer at 1000 rpm. Dissolve 2.7 g of lidocaine hydrochloride in 75.3 g of distilled water, then add to the Aquasorb A 380/propylene glycol slurry and mix for a further 2 hours with an overhead stirrer at 1000–1200 rpm, whilst maintaining the sample at a temperature of less than 15° C. Remove sample to centrifuge tubes and centrifuge at 4000 rpm for 2 hours.

By w/w, the thus obtained formulation equates to 1.7%, 13.8%, 17.2%, 2.0% and 64.9% of the cross-linked CMC, poloxamer 407, propylene glycol, lidocaine and water respectively.

EXAMPLE 9

Preparation of Wound Gel Containing Tea Tree Oil

Tea tree oil is the oil of *Melaleuca alternifolia*, and is a naturally sourced antiseptic having germicidal and antifungal properties. It is hydrophobic.

Formulation a)

A 116 g batch of product is prepared as follows:

Slurry 2 g of Aquasorb A380 in a mixture of 20 g of propylene glycol and 1.2 g of Tea tree oil by mixing for 10 minutes with overhead stirrer at 1000 rpm. Add 16 g of poloxamer P407 and continue mixing for a further 10 minutes with overhead stirrer at 1000 rpm. Add 76.8 g of distilled water and mix for a further 2 hours with an overhead stirrer at 1000–1200 rpm, whilst maintaining the sample at a temperature of less than 15° C. Remove sample to centrifuge tubes and centrifuge at 4000 rpm for 2 hours.

By w/w, the thus obtained formulation equates to 1.7%, 17.2%, 17.2%, 1.0% and 66.2% of the cross-linked CMC, poloxamer 407, propylene glycol, Tea tree oil and water respectively.

Formulation b)

A 116 g batch of product is prepared as follows:

Slurry 2 g of Aquasorb A380 in a mixture of 20 g of propylene glycol and 0.1 g of Tea tree oil by mixing for 10 minutes with overhead stirrer at 1000 rpm. Add 16 g of poloxamer P407 and continue mixing for a further 10 minutes with overhead stirrer at 1000 rpm. Add 77.9 g of distilled water and mix for a further 2 hours with an overhead stirrer at 1000–1200 rpm, whilst maintaining the sample at a temperature of less than 15° C. Remove sample to centrifuge tubes and centrifuge at 4000 rpm for 2 hours.

By w/w, the thus obtained formulation equates to 1.7%, 17.2%, 17.2%, 0.1% and 67.2% of the cross-linked CMC, poloxamer 407, propylene glycol, Tea tree oil and water respectively.

The invention claimed is:

1. A hydrogel comprising a pre-crosslinked gellant, water, and a poloxamer, wherein the concentration of said poloxamer is between 10 and 25% by weight of the hydrogel and the gellant comprises at least one cross-linked, superabsorbent polysaccharide, said hydrogel exhibiting thermally induced viscosification at a temperature between ambient and 35° C., and wherein said hydrogel has the capacity to absorb at least 50% further water in addition to the water already present.

2. A hydrogel according to claim 1 which has the capacity to absorb at least a further 150% water.

3. A hydrogel according to claim 1 which has the capacity to absorb at least twice its own weight of wound exudates.

4. A hydrogel according to claim 1 wherein the gellant comprises cross-linked starch, or a sodium salt thereof.

5. A hydrogel according to claim 4 wherein the gellant is the superabsorbent sodium salt.

6. A hydrogel according to claim 1 wherein the gellant comprises cross-linked carboxymethylcellulose, or a sodium salt thereof.

7. A hydrogel according to claim 6 wherein the gellant is the superabsorbent sodium salt.

8. A hydrogel according to claim 1 wherein the gellant is present in amount of 1 to 2.5% by weight of the hydrogel.

9. A hydrogel according to claim 1 comprising a combination of one or more poloxamers.

10. A hydrogel according to claim 9 wherein said one or more poloxamers of said combination are selected from the group consisting of F127, F108, F88, P188 or F98, and any mixture thereof.

11. A hydrogel according to claim 1 which comprises a poloxamer selected from the group consisting of F127, F108, F88, F87, P188, F98 and any mixture thereof.

12. A hydrogel according to claim 1 wherein the concentration of said poloxamer is between 10 and 20% by weight of the hydrogel.

13. A hydrogel according to claim 1 which further comprises a co-solvent.

14. A hydrogel according to claim 13 wherein the co-solvent is propylene glycol.

15. A hydrogel according to claim 1 comprising no further pharmaceutically active agent.

16. A hydrogel according to claim 1 which further comprises a therapeutically active agent.

17. A hydrogel according to claim 16 wherein the therapeutically active agent is hydrophobic.

18. A hydrogel according to claim 16 wherein the therapeutically active agent is selected from the group consisting of antibacterial agents, anaesthetics, analgesics, anti-inflammatory agents, growth factors, autologous cells, cellular matrix components, enzymes for debridement, and genes for gene therapy.

19. A hydrogel according to claim 18 wherein the agent is hydrophobic.

20. A hydrogel according to claim 16 wherein the therapeutically active agent is delivered in a sustained release manner.

21. A hydrogel according to claim 1 which is capable of absorbing moisture from all wound types.

22. A method for the treatment of an epithelial lesion on the human or animal body comprising applying to said lesion a hydrogel comprising a pre-crosslinked gellant, water, and a poloxamer, wherein the concentration of said poloxamer is between 10 and 25% by weight of the hydrogel and the gellant comprises at least one cross-linked, superabsorbent polysaccharide, said hydrogel exhibiting thermally induced viscosification at a temperature between ambient and 35° C., and wherein said hydrogel has the capacity to absorb at least 50% further water in addition to the water already present.

23. A method for the treatment of skin lesions selected from the group consisting of dry necrotic wounds, acute wounds, exudating wounds, burns, and infected wounds comprising applying to said lesion a hydrogel comprising a pre-crosslinked gellant, water, and a poloxamer, wherein the concentration of said poloxamer is between 10 and 25% by weight of the hydrogel and the gellant comprises at least one cross-linked, superabsorbent polysaccharide, said hydrogel exhibiting thermally induced viscosification at a temperature between ambient and 35° C., and wherein said hydrogel has the capacity to absorb at least 50% further water in addition to the water already present.

24. A syringe, bellow pack or a multidose system comprising a hydrogel according to claim 1.

25. A single dose delivery system comprising a hydrogel according to claim 1.

26. A pressurized delivery system comprising a hydrogel according to claim 1 capable for forming a spray upon release of pressure therefrom.

27. A composition comprising a pre-crosslinked gellant, the gellant comprising at least one cross-linked, superabsorbent polysaccharide, and a poloxamer suitable to be diluted with water to form a hydrogel according to claim 1.

28. A composition according to claim 27 wherein the poloxamer is F127, F108, F88, F87, P188, F98 or any mixture thereof.

* * * * *